(12) United States Patent
Ayotte et al.

(10) Patent No.: US 10,200,016 B2
(45) Date of Patent: Feb. 5, 2019

(54) CONTACTLESS READABLE PROGRAMMABLE TRANSPONDER TO MONITOR CHIP JOIN

(71) Applicant: INTERNATIONAL BUSINESS MACHINES CORPORATION, Armonk, NY (US)

(72) Inventors: Stephen P. Ayotte, New Haven, VT (US); Shawn P. Fetterolf, Cornwall, VT (US); Adam J. McPadden, Underhill, VT (US); Timothy M. Sullivan, Essex, VT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/691,262

(22) Filed: Aug. 30, 2017

(65) Prior Publication Data

US 2017/0366172 A1 Dec. 21, 2017

Related U.S. Application Data

(63) Continuation of application No. 14/039,744, filed on Sep. 27, 2013, now Pat. No. 9,876,487.

(51) Int. Cl.
| | | |
|---|---|---|
| *H01L 21/00* | (2006.01) | |
| *H03K 3/03* | (2006.01) | |
| *G01N 1/00* | (2006.01) | |
| *G01R 1/00* | (2006.01) | |
| *B23K 1/00* | (2006.01) | |
| *G01L 1/00* | (2006.01) | |

(52) U.S. Cl.
CPC .............. *H03K 3/0315* (2013.01); *B23K 1/00* (2013.01); *G01L 1/00* (2013.01); *G01N 1/00* (2013.01); *G01R 1/00* (2013.01); *H01L 21/00* (2013.01); *H01L 2221/00* (2013.01)

(58) Field of Classification Search
CPC ....... H01L 21/00; H01L 2221/00; G01L 1/00; G01L 7/00; B23K 1/00
See application file for complete search history.

(56) References Cited

U.S. PATENT DOCUMENTS

| | | | |
|---|---|---|---|
| 3,014,364 A | | 12/1961 | Crooks |
| 4,984,730 A | * | 1/1991 | Gobel .................. B23K 20/004 228/1.1 |
| 5,490,182 A | | 2/1996 | Arai |
| 5,533,398 A | * | 7/1996 | Sakurai ................. G01L 5/0038 73/573 |

(Continued)

OTHER PUBLICATIONS

Notice of Allowance in related U.S. Appl. No. 14/039,744 dated Sep. 12, 2017, 8 pages.

(Continued)

*Primary Examiner* — Jermele M Hollington
*Assistant Examiner* — Temilade Rhodes-Vivour
(74) *Attorney, Agent, or Firm* — Steven Meyers; Andrew M. Calderon; Roberts Mlotkowski Safran Cole & Calderon, P.C.

(57) ABSTRACT

A contactless readable programmable transponder to monitor chip join and method of use are disclosed. The method includes reading a frequency of an oscillator associated with a chip module. The method further includes correlating the frequency with a bond quality of the chip module.

5 Claims, 5 Drawing Sheets

(56) References Cited

U.S. PATENT DOCUMENTS

| | | | |
|---|---|---|---|
| 5,939,950 A | 8/1999 | Kamei | |
| 5,956,659 A | 9/1999 | Spies et al. | |
| 5,959,875 A | 9/1999 | Kawahara et al. | |
| 6,337,906 B1 | 1/2002 | Bugash et al. | |
| 6,458,623 B1 | 10/2002 | Goldmann et al. | |
| 6,891,110 B1 | 5/2005 | Pennaz et al. | |
| 6,906,425 B2 | 6/2005 | Stewart et al. | |
| 7,423,547 B2 | 9/2008 | Pavlovic et al. | |
| 7,439,158 B2* | 10/2008 | Forbes | H01L 21/76254 257/E21.568 |
| 7,548,823 B2 | 6/2009 | Singh et al. | |
| 7,889,013 B2 | 2/2011 | Leatherman et al. | |
| 7,977,962 B2 | 7/2011 | Hargan et al. | |
| 8,273,610 B2 | 9/2012 | Or-Bach et al. | |
| 2008/0061894 A1 | 3/2008 | Raita et al. | |
| 2008/0204055 A1 | 8/2008 | Pagani | |
| 2010/0065851 A1* | 3/2010 | Makita | H01L 27/12 257/72 |
| 2011/0006794 A1 | 1/2011 | Sellathamby et al. | |
| 2011/0027930 A1 | 2/2011 | El-Gamal et al. | |
| 2011/0310381 A1 | 12/2011 | Kamata | |
| 2012/0032354 A1* | 2/2012 | Pham | B23K 20/007 257/784 |
| 2012/0049299 A1* | 3/2012 | Chou | B81C 1/00246 257/417 |
| 2012/0297884 A1 | 11/2012 | Gamage et al. | |
| 2014/0184262 A1 | 7/2014 | Poindexter et al. | |

OTHER PUBLICATIONS

Office Action in related U.S. Appl. No. 16/105,600 dated Oct. 19, 2018, 11 pages.

\* cited by examiner

CONTACTLESS READABLE PROGRAMMABLE TRANSPONDER TO MONITOR CHIP JOIN

FIELD OF THE INVENTION

The invention relates to semiconductor structures and, more particularly, to a contactless readable programmable transponder to monitor chip join and method of use.

BACKGROUND

During module assembly the process of joining a silicon die (device) to the substrate (chip carrier) involves creating a metallurgical joint between solder connections, e.g., controlled collapse chip connections (C4s), and the chip carrier. Defects, though, can occur during this joining process, known as non-contact non-wet (no contact between metallurgical joint) and contact non-wet (some electrical contact), resulting in failure to make the required conductive metallurgical joint. The most common location of C4 non wets is the highest DNP, distance to neutral point, or farthest location from the center of the chip. These defects occur more often in lead free C4s, 50 micron C4s, and coreless laminates.

Currently, chip join effectiveness is monitored by post chip join side inspection. Although this can be effective in certain instances, this method is limited to only the first few rows from the edge of the chip carrier. By way of example, an approach to monitoring chip join effectiveness is chip pull or chip shear. This type of testing is a destructive test. Accordingly, even if it is found that the chip connections (e.g., C4s) have all joined well, it is still necessary to discard the module. Also, opens at module test can be evaluated for the presence of C4 non wets but at that point it is many operations away from the chip join process and knowing what specific parameters about the process that may have lead to the condition is more difficult.

In addition, due to CTE (coefficient of thermal expansion) mismatch a fundamental technology issue requires the use of certain techniques to address the chip join problem in an iterative fashion. These techniques can include compensated laminates, compensated silicon or both.

Specific process conditions can also influence the factors that affect the formation of non wets (which results in failure to make a conductive metallurgical join), e.g., controlled ramp rates or cool downs. Again the effectiveness of these process changes cannot be fully known until the module (e.g., die and chip carrier) has been completed through assembly and tested.

Accordingly, there exists a need in the art to overcome the deficiencies and limitations described hereinabove.

SUMMARY

In an aspect of the invention, a method comprises reading a frequency of an oscillator associated with a chip module. The method further comprises correlating the frequency with a bond quality of the chip module.

In an aspect of the invention, a method comprises completing circuitry of a wireless transponder and ring oscillator by bonding a device substrate to a chip carrier.

In an aspect of the invention, a chip module comprises: a device substrate; a chip carrier; solder connections between the device substrate and the chip carrier; circuitry on at least one of the device substrate and the chip carrier forming a wireless transponder associated with the chip module; and circuitry on both the device substrate and the chip carrier forming a ring oscillator associated with the chip module.

In another aspect of the invention, a design structure tangibly embodied in a machine readable storage medium for designing, manufacturing, or testing an integrated circuit is provided. The design structure comprises the structures of the present invention. In further embodiments, a hardware description language (HDL) design structure encoded on a machine-readable data storage medium comprises elements that when processed in a computer-aided design system generates a machine-executable representation of the contactless readable programmable transponder to monitor chip join, which comprises the structures of the present invention. In still further embodiments, a method in a computer-aided design system is provided for generating a functional design model of the contactless readable programmable transponder to monitor chip join. The method comprises generating a functional representation of the structural elements of the contactless readable programmable transponder to monitor chip join.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

Figure 1:
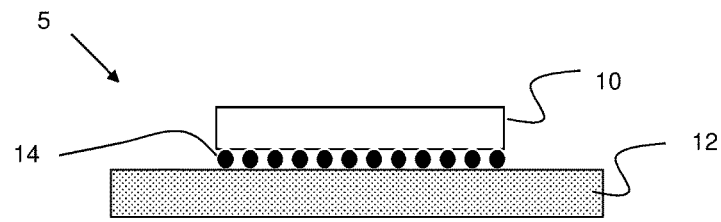
FIG. 1 shows a module in accordance with aspects of the present invention.

The invention relates to semiconductor structures and, more particularly, to a contactless readable programmable transponder to monitor chip join in a module and method of use. More specifically, the present invention incorporates active or passive RFID devices, chiplets and antennas into subcomponents associated with a module build, e.g., joining of a device to a chip carrier. Advantageously, in embodiments, the present invention utilizes design space in the device substrate (die) and/or chip carrier in order to provide chiplets, e.g., electrical contacts, in very specific locations, e.g., corners of the die. The additional design space can also include, for example, components for an integrated and functional contactless readable programmable transponder. The components of the contactless readable programmable transponder can be completed upon module build, e.g., chip joining.

By using the contactless readable programmable transponder, it is possible to utilize a passive RFID reader to query the chip immediately following chip join to determine how many of the chiplets are active, e.g., properly joined. By knowing the amount and location of the active chiplets, it is possible to determine if the chip join operation was successful in making high-quality metallurgical joints. Accordingly, it is now possible to provide immediate feedback of the chip join effectiveness in all of the locations where there is a chiplet connected to a C4.

As another benefit, the RFID can also be used to record important processing information. More specifically, the RFID can record the tool "ID" for each of the tools where a sequence or sublot process is utilized. Along with the tool "ID", date, time, shift, etc. can also be recorded. This information can be cumulative throughout the assembly process, allowing for pinpoint accuracy of the tools associated with the module build. This allows the engineer/technician to pinpoint the specific tool, time, etc. when a specific process defect is found. Also, through the utilization of RFID readers, it is now possible to track a module through any process and know exactly where all components are at any given time.

In addition, the RFID value can be associated with an ECID value programmed into the chip. By having an RFID tag built into the module with a cross correlation to the ECID, it is now only necessary to read the RFID value in order to be able to determine the original test data. The RFID tag could also have many other uses such as, for example, tracking of shipments, tracking of the population of parts such that if a recall was required on a set of RFID values, system level software (in which the RFID is integrated into) could be queried to determine where all of those RFID values were located, etc.

In one implementation, the device substrate and chip carrier each have connection points such that if the connections are not completed during the join processes (e.g., bonding operation of the module), a memory would not be connected to the RFID tag, and nothing can be read. In operation, if the RFID tag does not work, e.g., cannot be read, it will be assumed that the chip join process failed or that there is a poor quality of bonding of the module. This solves the problem of knowing that modules need rework at the original bonding operation.

In another implementation, the connection points can form a ring oscillator and memory block of an RFID tag. In this embodiment, the memory block can contain the chip ID information/processing information, etc. In use, the complete connection of the ring oscillator (and connection points) occurs only with a good chip join connection. By way of example, in operation, when the stand-alone tag works, it will be possible to obtain a response to a query of the ID and to measure a frequency of the ring oscillator. In this implementation the following scenarios can occur:

(i) The memory cannot be read and the tag is broken: In this scenario, chip join is likely a fail;

(ii) The memory is read and the frequency of the ring oscillator is not read: In this scenario, the tag works, but the ring oscillator is assumed to not be properly connected during the join process. Accordingly, it is assumed that the chip join process is a likely fail;

(iii) The memory is read and the frequency of the ring oscillator is measured but not as expected: In this scenario, the ring oscillator has bad connections (e.g., bad connection from top to bottom or a bad inverter). Accordingly, it is assumed that the chip join process is a likely fail; and (iv) The tag works and the frequency of the ring oscillator is measured as expected: In this scenario, chip join is assumed to be good (e.g., connections of C4s are good) and the product is ready for shipment.

In further implementations, the memory block and RFID tag architecture can be completely located on the device substrate or chip carrier; whereas, in another implementation, the memory block can be located on either the device substrate or chip carrier. In the first implementation, the chip ID/process information and access to it can be provided regardless of the quality of bonding. In the second implementation, chip ID/process information and access thereto only exists when there is good bonding. In these implementations the following scenarios can occur:

(i) The tag works but the memory is not addressable: In this scenario, it is assumed that a poor quality bond exists; or (ii) The tag works and the memory is addressable: In this scenario, a good bond exists. In this scenario, it may be difficult to assess bonding quality, but it is still possible to perform debugging to determine if the bonding is bad in a particular way depending on how the connections to the memory are made, e.g., regional bonding issues might be detectable. In other words, if the signals to/from the array are spread out across the available area and the signals are placed intelligently, the manner in which the memory is not working could provide a clue as to where/how the bonding did not work.

In further implementations, a line is provided from a logic controller to the memory block. In this implementation, it is possible to tell the RFID tag to read the memory directly or through another path, i.e., through the bonds alternately. This solution preserves both the ability to read the chip ID and process information in the memory, as well as verify the bonding.

FIG. 1 shows a module 5 in accordance with aspects of the present invention. More specifically, the module 5 comprises a device substrate (die) 10 bonded to a chip carrier 12. In embodiments, the device substrate 10 is bonded to the chip carrier through electrical connections 14. The electrical connections 14 can be, for example, C4 connections. The electrical connections 14 can also be representative of chiplets, RFID architectures, memory, logic, and other circuitry, in accordance with aspects of the present invention. As should be understood by those of skill in the art, C4 is a method for interconnecting semiconductor devices, such as IC chips to external circuitry with solder bumps that have been deposited onto chip pads.

Figure 2:
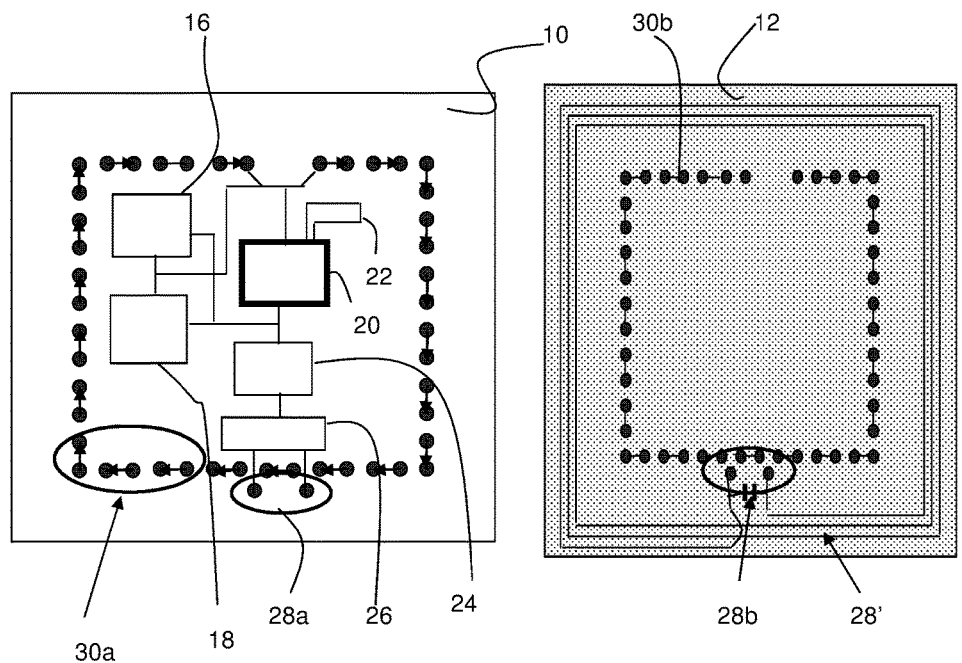
FIG. 2 shows the components of the module of FIG. 1, in accordance with aspects of the present invention.

FIG. 2 shows the components of the module of FIG. 1, in accordance with aspects of the present invention. More specifically, the device substrate 10 (e.g., silicon die) comprises circuitry (including the architecture for an RFID tag) and connection pads. In particular, the circuitry includes memory block 16, logic controller 18, ring oscillator measurement block 20 with a reference loop 22, a voltage regulator 24, a charge pump/modulator demodulator 26 and antenna connection 28a. As should be understood by those of skill in the art, the functional contact-less readable/programmable transponder logic can comprises the memory block 16, logic controller 18, voltage regulator 24, and charge pump/modulator demodulator 26.

In embodiments, the connection pads are electrical connections, with integrated inverters 30a, e.g., two FETs, connecting to every other pair of connection pads. As should be understood by those of skill in the art, the integrated inverters 30a can vary between the device substrate 10 and the chip carrier 12 in any N+1 configuration. For example, N number of inverters can be provided on the device substrate 10 and N+1 number of inverters can be provided on the chip carrier 12, resulting in 2N+1 inverters. In embodiments, when the chip module is correctly joined, e.g., when the device substrate 10 is joined to the chip carrier 12, the N+1 inverters and connection pads form a ring oscillator. It should also be understood by those of skill in the art that the circuitry and/or any of the components in any of the embodiments can be formed exclusively on the device substrate 10 and/or the chip carrier 12 or any combination thereof, providing that the joining process can result in an electrical connection of such circuitry and/or components to monitor the quality of chip join.

In embodiments, the memory block 16 can be any type of programmable non-volatile memory. For example, the memory block 16 can be EEPROM; although, other memory blocks are also contemplated by the present invention. In embodiments, the memory block 16 can be divided into two different memory blocks: (i) one memory block (address space) can always be readable in order to maintain tracking benefits, and (ii) one memory block (address space) is only readable when the join process has been successful allowing for join quality assessment. In operation, the memory block 16 can record tool ID, shift, date, time, etc, which can be read at any step in the process.

The logic controller 18 can be connected to the memory block 16. In operation, the logic controller 18 decodes incoming logical command (read/write/measure/ . . . ), and produces signals to other blocks as should be understood by those of skill in the art. For example, the logic controller 18 can read and write, and send read and write commands to the memory block 16. Also, the logic controller 18 can execute a reset of the ring oscillator, inject a seed signal, and force a measurement of the frequency of the ring oscillator. The reference loop 22 can be used to provide a comparison reference.

Still referring to FIG. 2, the chip carrier 12 includes an integrated antenna 28' and an antenna connection 28b. The chip carrier 12 also includes a plurality of connection pads with a wiring having certain resistance and capacitance, designated at reference numeral 30b. The plurality of connection pads and wiring 30b are complementary to the connection pads 30a of the device substrate 10, which upon a properly joined module forms the ring oscillator. The capacitance of the plurality of connection pads with wiring 30b can be matched to complete the resonant circuit with the integrated antenna 28' (i.e., tuned to the transmission frequency). In embodiments, the integrated antenna 28' is designed for maximum read frequency sensitivity/power harvesting and tuned to the transmission frequency.

In this configuration, when the device substrate 10 is bonded to the chip carrier 12, the connection pads 30b are electrically connected to the connection pads 30a (to form the ring oscillator), and the antenna connection 28b is electrically connected to the antenna connection 28a. In this way, the integrated antenna 28' can be connected to the components (circuitry) of the device substrate 10, which completes the contactless reader transponder. The integrated antenna 28' can then be used to wirelessly broadcast information, e.g., from the memory block, frequency from the ring oscillator, etc.

In operation, using a reading device at a specific selected and tuned frequency, e.g., matched to the contact-less readable/programmable transponders frequency range, it is now possible to monitor the quality of the chip join process by polling the transponder to return a measured frequency of the ring-oscillator and as a result have a measure of chip join effectiveness for non wets. The following scenarios can be used to determine the quality of the bond between the device substrate 10 and the chip carrier 12:

(i) The frequency of the ring oscillator is measured but not as expected (e.g., cannot be read): In this scenario, the ring oscillator has bad connections (e.g., bad connection from top to bottom or a bad inverter), and it can be thus assumed that the chip join process is a likely fail. Thus, incorrect read values represent unreliable contacts; and (ii) The frequency of the ring oscillator is measured as expected: In this scenario, it can be thus assumed that the chip join process was successful and the product is ready for shipment.

In this way, it is now possible to provide immediate detection of misconnected components at chip join, with an invalid or bad frequency measurement implying a poor quality or bad connection. This, in turn, enables rework to "recover" the misconnected device; whereas, rework is not possible after underfill has been added to the assembly.

Figure 3:
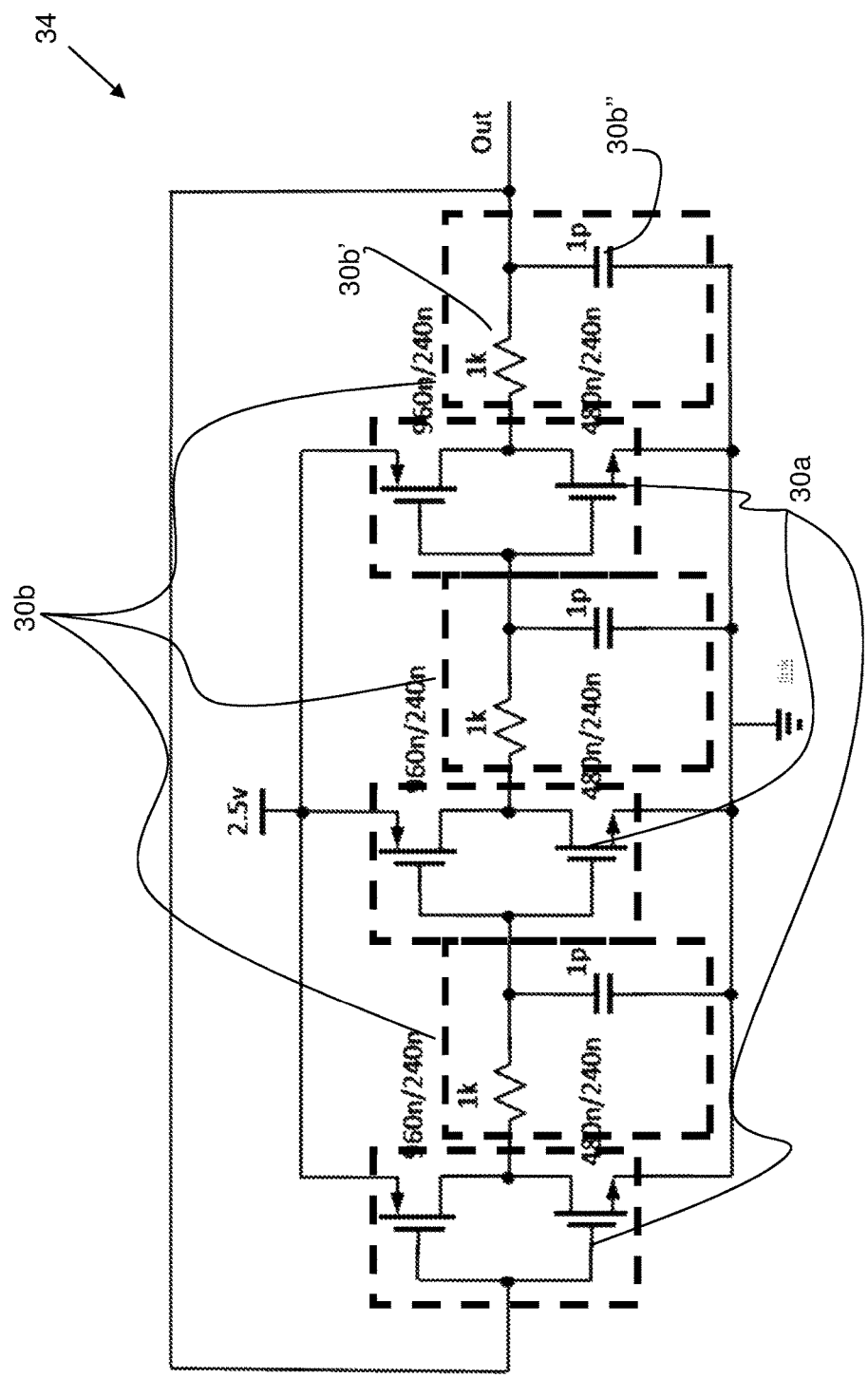
FIG. 3 shows an N-stage ring oscillator used with a contactless readable programmable transponder to monitor chip join in accordance with aspects of the present invention.

FIG. 3 shows an N-stage ring oscillator 34 used with the contactless readable programmable transponder in accordance with aspects of the present invention. In embodiments, the N-stage ring oscillator 34 includes the connection pads with integrated inverters 30a, e.g., two FETs, and the plurality of connection pads with wiring 30b. As should be understood by those of skill in the art, the plurality of connection pads with wiring 30b include a resistor 30b' and a capacitor 30b", each of which can be any designed value. In embodiments, the integrated inverters 30a, e.g., two FETs, can be located on either the device substrate 10 or the chip carrier 12; whereas, the complementary connection pads 30b can be located on the chip carrier 12 or the device substrate 10, respectively. In either scenario, a quality bond of the chip carrier 12 to the device substrate 10 will result in a fully functional ring oscillator, which can be used to assess chip join quality. In operation of the N-stage ring oscillator 34:

(i) The transistors will power up 50% on and 50% off in an ideal case; and (ii) Reset will turn off all transistors, then turn them all back on again.

By using the N-stage ring oscillator 34, it is possible to determine a quality of the bond between the device substrate 10 and the chip carrier 12 by matching a characteristic frequency of the the N-stage ring oscillator 34 with a frequency associated with a bond quality. For example, the characteristic frequency of the the N-stage ring oscillator 34 can be correlated to a known physical quality of the bond to determine bond quality. By way of illustrative example, a characteristic frequency #1 can be correlated to a good bond quality (e.g., low electrical resistance of the bond) and a characteristic frequency #2 can be correlated to a poor bond quality (e.g., high electrical resistance of the bond). Advantageously, these characteristic frequencies can be read remotely (wirelessly), using the RFID tag.

Figure 4:
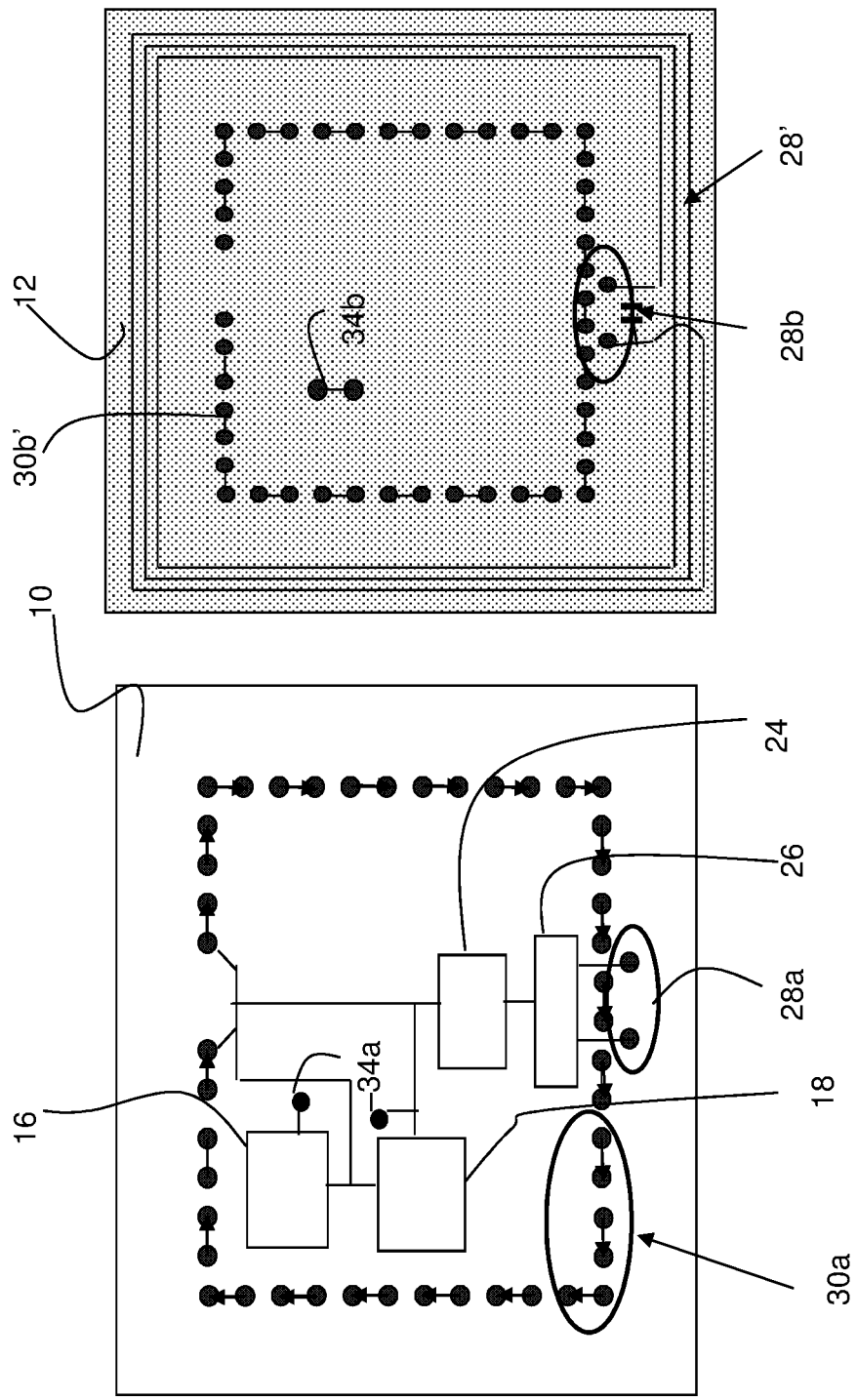
FIG. 4 shows another variation of the module of FIG. 1, in accordance with aspects of the present invention.

FIG. 4 shows another variation of the module of FIG. 1, in accordance with aspects of the present invention. In this aspect of the invention, the memory block 16 of the device substrate 10 includes two connection pads 34a which correlate to complementary connection pads 34b on the chip carrier 12. In a chip join process, the two connection pads 34a will electrically couple to the connection pads 34b, completing the circuit. The complete circuit will be indicative of a quality chip join. That is, in a quality chip join process, the memory block will be electrically coupled to the remaining portions of the transponder logic, thus completing the contact-less readable transponder.

As with the previous aspect of the invention, in the implementation of the module of FIG. 4, by using an RFID reading device at a specific selected and tuned frequency, carefully matched to the contact-less readable/programmable transponders frequency range, it is now possible to monitor the quality of chip join process by polling the transponder to return the stored memory value and as a result have a measure of join effectiveness. For example, an incorrect read value will represent unreliable contacts (missing connections between the memory and the remainder of the transponder will result in incorrect responses); whereas, a correct read value will represent reliable contacts and a quality join process. In addition, it is also assumed that a reliable contact and hence quality join process is provided when the memory can be read.

Figure 5:
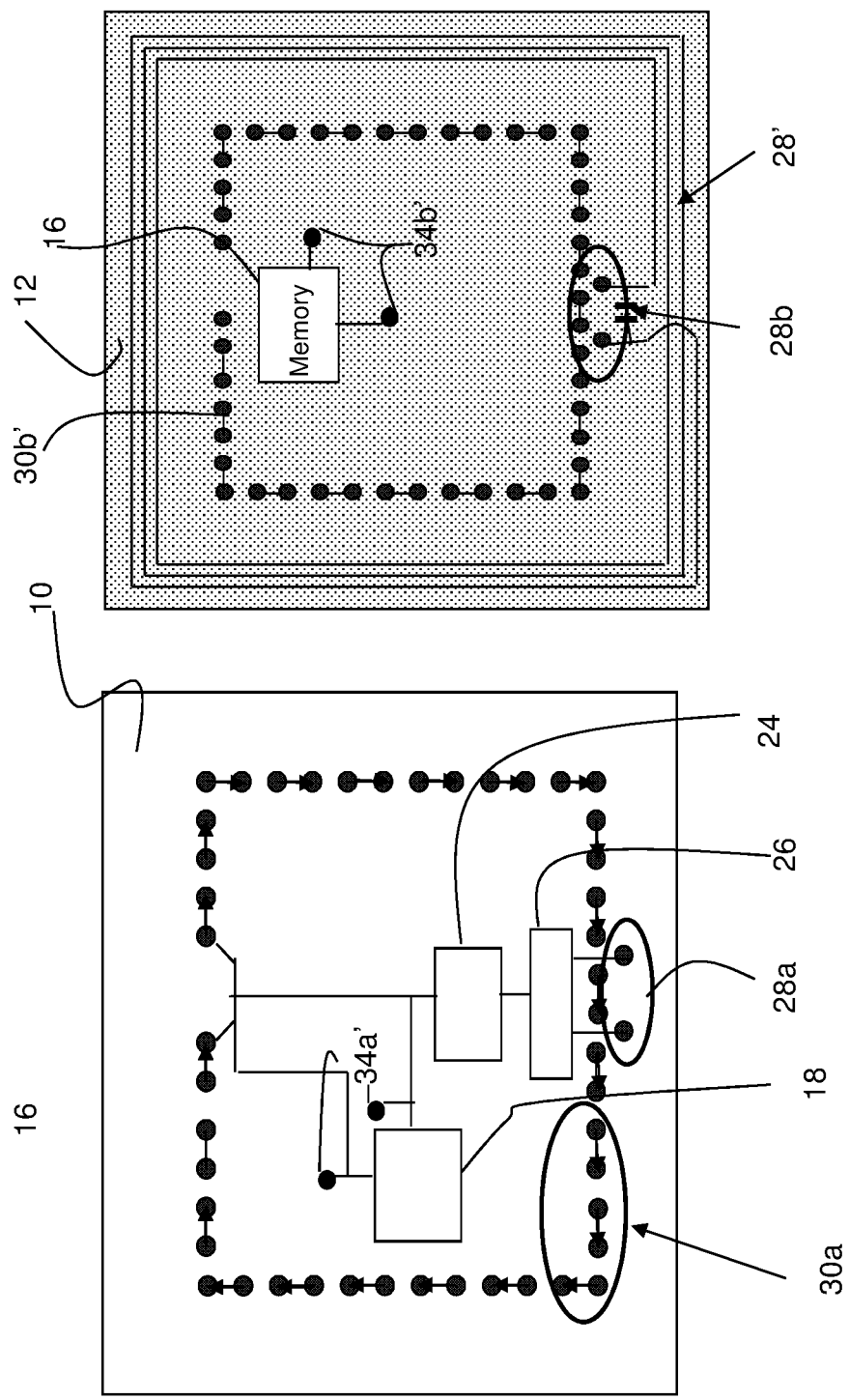
FIG. 5 shows yet another variation of the module of FIG. 1, in accordance with aspects of the present invention.

FIG. 5 shows yet another variation of the module of FIG. 1, in accordance with aspects of the present invention. In this aspect of the invention, the memory block 16 and two connection pads 34b' are provided on the chip carrier 12, with the remaining circuitry and complementary connection pads 34a' being provided on the device substrate 10. In a chip join process, the two connection pads 34a' will electrically couple to the connection pads 34b', completing the circuit. In a quality chip join process, the memory block will be electrically coupled to the remaining portions of the transponder logic, thus completing the contact-less readable transponder. As in any of the embodiments, careful placement of integration connection points can be used to monitor critical chip join areas (areas with problems).

Figure 6:
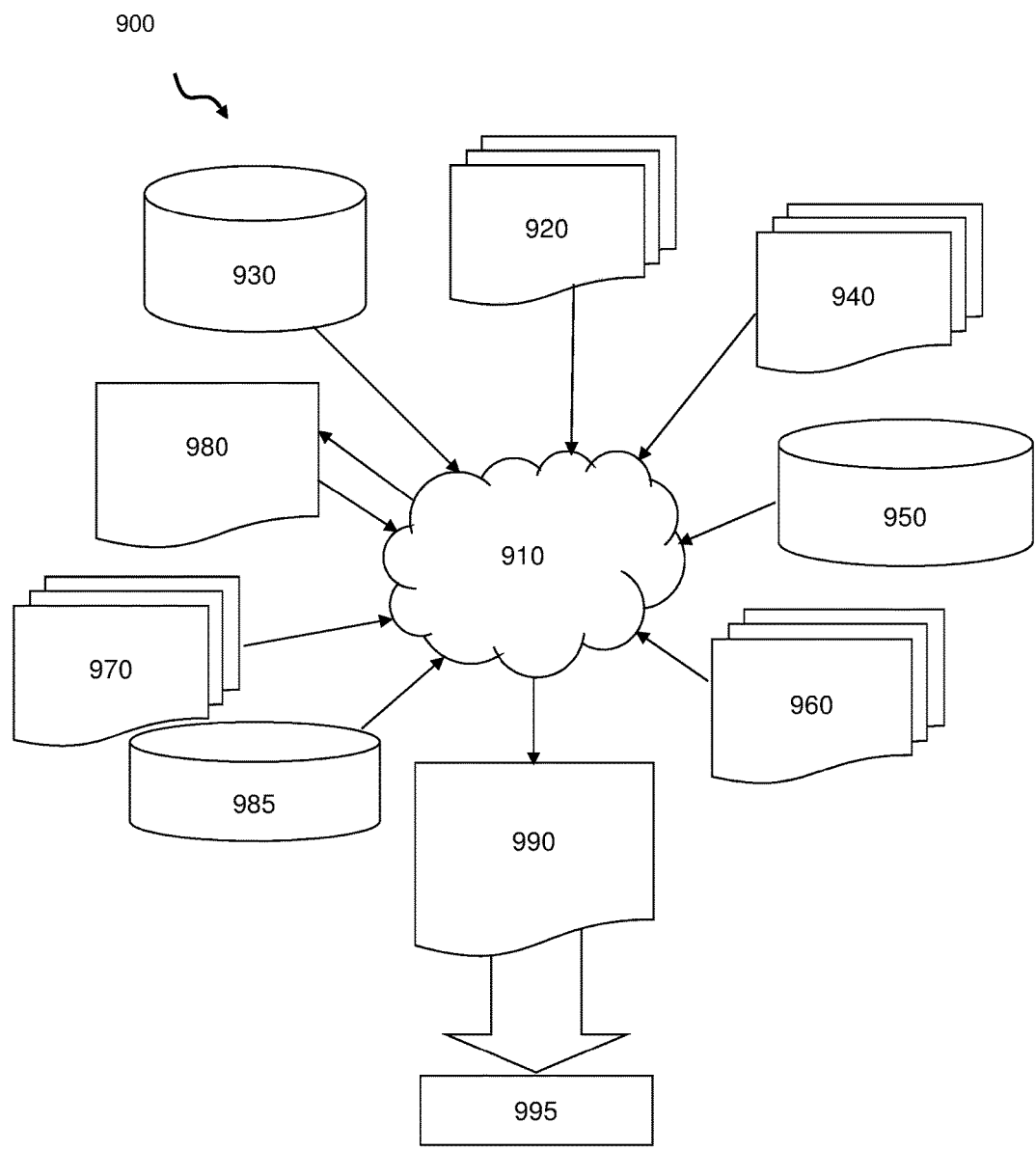
FIG. 6 is a flow diagram of a design process used in semiconductor design, manufacture, and/or test.

FIG. 6 is a flow diagram of a design process used in semiconductor design, manufacture, and/or test. FIG. 6 shows a block diagram of an exemplary design flow 900 used for example, in semiconductor IC logic design, simulation, test, layout, and manufacture. Design flow 900 includes processes, machines and/or mechanisms for processing design structures or devices to generate logically or otherwise functionally equivalent representations of the design structures and/or devices described above and shown in FIGS. 1-5. The design structures processed and/or generated by design flow 900 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 6 illustrates multiple such design structures including an input design structure 920 that is preferably processed by a design process 910. Design structure 920 may be a logical simulation design structure generated and processed by design process 910 to produce a logically equivalent functional representation of a hardware device. Design structure 920 may also or alternatively comprise data and/or program instructions that when processed by design process 910, generate a functional representation of the physical structure of a hardware device. Whether representing functional and/or structural design features, design structure 920 may be generated using electronic computer-aided design (ECAD) such as implemented by a core developer/designer. When encoded on a machine-readable data transmission, gate array, or storage medium, design structure 920 may be accessed and processed by one or more hardware and/or software modules within design process 910 to simulate or otherwise functionally represent an electronic component, circuit, electronic or logic module, apparatus, device, or system such as those shown in FIGS. 1-5. As such, design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 910 preferably employs and incorporates hardware and/or software modules for synthesizing, translating, or otherwise processing a design/simulation functional equivalent of the components, circuits, devices, or logic structures shown in FIGS. 1-5 to generate a netlist 980 which may contain design structures such as design structure 920. Netlist 980 may comprise, for example, compiled or otherwise processed data structures representing a list of wires, discrete components, logic gates, control circuits, I/O devices, models, etc. that describes the connections to other elements and circuits in an integrated circuit design. Netlist 980 may be synthesized using an iterative process in which netlist 980 is resynthesized one or more times depending on design specifications and parameters for the device. As with other design structure types described herein, netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 910 may include hardware and software modules for processing a variety of input data structure types including netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. Design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 910 without deviating from the scope and spirit of the invention. Design process 910 may also include modules for performing standard circuit design processes such as timing analysis, verification, design rule checking, place and route operations, etc.

Design process 910 employs and incorporates logic and physical design tools such as HDL compilers and simulation model build tools to process design structure 920 together with some or all of the depicted supporting data structures along with any additional mechanical design or data (if applicable), to generate a second design structure 990.

Design structure 990 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 920, design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1-5. In one embodiment, design structure 990 may comprise a compiled, executable HDL simulation model that functionally simulates the devices shown in FIGS. 1-5.

Design structure 990 may also employ a data format used for the exchange of layout data of integrated circuits and/or symbolic data format (e.g. information stored in a GDSII (GDS2), GL1, OASIS, map files, or any other suitable format for storing such design data structures). Design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1-5. Design structure 990 may then proceed to a stage 995 where, for example, design structure 990: proceeds to tape-out, is released to manufacturing, is released to a mask house, is sent to another design house, is sent back to the customer, etc.

The method(s) as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chip module, comprising:
   a device substrate;
   a chip carrier;
   solder connections between the device substrate and the chip carrier;
   circuitry on at least one of the device substrate and the chip carrier forming a wireless transponder associated with the chip module; and
   circuitry on both the device substrate and the chip carrier forming a ring oscillator associated with the chip module,
   wherein the wireless transponder comprises a memory block of an RFID tag formed from connection points between the device substrate and chip carrier.

2. The chip module of claim 1, wherein the wireless transponder comprising the memory block is provided on one of the device substrate and the chip carrier with remaining circuitry of the wireless transponder on one of the chip carrier and the device substrate, respectively.

3. The chip module of claim 1, wherein the circuitry of the ring oscillator comprises a set of N+1 invertors on one of the device substrate and the chip carrier with wiring of a certain resistance and capacitance on one of the chip carrier and the device substrate, respectively.

4. The chip module of claim 1, further comprising an integrated antenna coupled to the wireless transponder when the chip module is joined.

5. The chip module of claim 1, wherein the transponder is a contactless readable programmable transponder which utilizes a passive RFID reader to query the chip module following chip join to determine how many chiplets are active and their location and the memory block is structured to record chip information including at least one of chip identification, tool identification and cross correlation to an ECID value programmed into the chip module.

* * * * *